(12) United States Patent
Wilkins

(10) Patent No.: US 8,431,144 B2
(45) Date of Patent: Apr. 30, 2013

(54) ANIMAL DETERRENT FOR PROTECTING PLANTS

(76) Inventor: Tracy D. Wilkins, Riner, VA (US)

( * ) Notice: Subject to any disclaimer, the term of this patent is extended or adjusted under 35 U.S.C. 154(b) by 610 days.

(21) Appl. No.: 12/484,055

(22) Filed: Jun. 12, 2009

(65) Prior Publication Data

US 2009/0252776 A1    Oct. 8, 2009

Related U.S. Application Data

(63) Continuation of application No. 10/902,103, filed on Jul. 30, 2004, now abandoned.

(51) Int. Cl.
*A01N 25/24* (2006.01)
*A01N 25/00* (2006.01)
*A61K 9/14* (2006.01)
*A61K 33/00* (2006.01)

(52) U.S. Cl.
USPC ........... 424/407; 424/405; 424/498; 424/724; 514/920

(58) Field of Classification Search .................. 424/405, 424/507, 489, 600, 617, 724; 514/918–920; 504/100–367
See application file for complete search history.

(56) References Cited

U.S. PATENT DOCUMENTS

| | | | |
|---|---|---|---|
| 3,089,280 A | 5/1963 | Klaas | |
| 3,120,445 A | 2/1964 | Aluisi et al. | |
| 3,962,425 A | 6/1976 | Oita et al. | |
| 3,980,773 A | 9/1976 | Oh et al. | |
| 4,065,576 A | 12/1977 | Oita et al. | |
| 4,065,577 A | 12/1977 | Oita et al. | |
| 4,965,070 A | 10/1990 | Messina | |
| 5,009,192 A | 4/1991 | Burman | |
| 5,326,573 A | 7/1994 | Antfang et al. | |
| 5,698,191 A | 12/1997 | Wiersma et al. | |
| 5,892,446 A | 4/1999 | Reich | |
| 6,464,995 B1 | 10/2002 | Sekutowski et al. | |
| 6,652,870 B2 | 11/2003 | Campbell et al. | |
| 2003/0198659 A1 | 10/2003 | Hoffmann et al. | |

FOREIGN PATENT DOCUMENTS

DE    3021693    * 12/1981

OTHER PUBLICATIONS

Herbivory, Wikipedia http://en.wikipedia.org/wiki/Herbivore, 2008.*
Rat control, http://www.birdandanimalcontrol.com, 2008.*
Gopher control, http://www.birdandanimalcontrol.com, 2008.*
Rabbit control, http://www.birdandanimalcontrol.com, 2008.*
Deer control, http://www.birdandanimalcontrol.com, 2008.*
USDA Natural Resources Conservation Service (NRCS) Soils, NSSH Part 618 (42-55) (no date); http://soils.usda.gov/technical/handbook/contents/part618p3.html.
Leeper et al., Soil Science: An Introduction. $5^{th}$ Ed. Melbourne U Pr. p. 123. 1993.
Potters Industries Inc. VISIBEAD, 2001.

* cited by examiner

*Primary Examiner* — Shengjun Wang
(74) *Attorney, Agent, or Firm* — Latimer IP Law, LLC

(57) ABSTRACT

The invention provides materials, compositions, methods, and kits for deterring or repelling animals from eating plant materials. The invention relates to the use of particulate matter to deter animals from eating plant materials that are susceptible to grazing by animals. In exemplary embodiments, an adhesive is applied to target plant material and the particulate matter is then applied prior to curing or drying of the adhesive.

5 Claims, No Drawings

ANIMAL DETERRENT FOR PROTECTING PLANTS

CROSS-REFERENCE TO RELATED APPLICATIONS

This application is a continuation application of U.S. patent application Ser. No. 10/902,103, filed 30 Jul. 2004 now abandoned, the entire disclosure of which is hereby incorporated herein in its entirety by reference.

BACKGROUND OF THE INVENTION

1. Field of the Invention

The present invention relates to the field of animal deterrents and repellents. More specifically, the present invention relates to compositions, methods, and kits for applying a substance to plants that repels animals or deters them from eating the plants.

2. Description of Related Art

Wildlife conservation efforts in rural areas, re-establishment or maintenance of wooded areas within suburban and urban tracts, and adaptation by wild animals to the presence of humans has resulted in a tremendous increase in the number of wild animals living in close proximity to human dwellings and agricultural and foresting areas in the past 20 years or so. Many of these animals are herbivores that thrive on the grasses, saplings, flowering plants, and fruits and vegetables planted and tended by humans. Indeed, the number of wild animals present in suburban and rural areas and commercial forestry areas, and the associated damage to trees, crops, and gardens, has increased to the point where many of these animals are widely considered pests.

Numerous compositions, devices, and methods have been devised to deter or repel wild animals, and in particular herbivores, from certain geographic areas. Typically, the compositions contain compounds that emit odors that are unpleasant (e.g., hydrogen sulfide or rotten eggs) or that are distasteful (e.g., hot pepper extracts). Commonly known devices include those that release unpleasant odors or distasteful substances, and those that emit unpleasant sounds or other stimuli that startle or annoy the animal.

For example, published U.S. patent application number US 2003/0198659 A1 discloses fibrous pest deterrents that comprise a non-woven fibrous matrix and a chemical deterrent. Such a combination is disclosed as providing both a physical and chemical deterrent. Among the pests deterred are deer and other herbivores. One of the many chemical deterrents disclosed is hydrogen sulfide, which is responsible for the offensive odor of rotten eggs.

Likewise, use of aliphatic aldehydes, which are thought to emit an unpleasant odor, as deterrents and repellants for ruminants is disclosed in U.S. Pat. No. 4,065,577. Similarly, U.S. Pat. No. 4,065,576 discloses the use of unsaturated aliphatic hydrocarbons as deterrents and repellents for ruminants. Upon oxidation, these unsaturated aliphatic hydrocarbons are converted to their corresponding aliphatic aldehydes, which are thought to emit an unpleasant odor. These patents disclose that it is not necessary for the ruminant to eat the plant matter that has been treated with the aliphatic aldehydes or precursors for the compositions to be effective.

In addition, a ruminant repellent comprising the putrescent product of a mixture of animal lipoidal material and a lipolytic enzyme is known from U.S. Pat. No. 3,962,425. This patent discloses that the putrescent material can be prepared in conjunction with a binder or "sticker" that causes the active agent to adhere to the edible portions of the plant to be treated. Suitable binders are disclosed as acrylic vinylacetate, acrylic ester polymers, acrylic co-polymers, and asphalt.

As an alternative to putrescent products, U.S. Pat. No. 3,980,773 discloses a ruminant deterrent that contains a phospholipid as an active ingredient. The patent discloses that the active ingredient can be combined with other substances, including a binder that increases the adherence of the repellent to the edible material after application. Suitable binders are disclosed as acrylic vinylacetate, acrylic co-polymers, and acrylic ester polymers. The patent indicates that an advantage of the invention is an extended shelf-life, which is about six months, based on the stability of the source of the phospholipids. As with other deterrents based on odor, it is not necessary for the ruminants to ingest the deterrent for it to be effective.

Further, compositions and methods for deterring animals are disclosed in U.S. Pat. No. 6,652,870. These compositions and methods rely on release of ammonia from shellfish waste that has been applied on or around plants that are typically damaged by herbivores. In practicing the invention, the shellfish waste is mixed with other ingredients and applied directly to the plants, to the ground around the base of the plants, or on paper strips placed near the plants. Because the repellent action is based on release of malodorous ammonia, ingestion of plant material is not required for the repellent effect.

Others have devised methods of deterrence based on applying a composition that renders the edible portions of plants offensive to the taste. For example, U.S. Pat. No. 4,965,070 discloses a composition for deterring deer that comprises liquid hot sauce containing hot peppers and tabasco peppers. The composition can be applied to plant surfaces that are subject to grazing by deer, and can include an adhesive to aid in adherence. In addition, U.S. Pat. No. 5,985,010 discloses the use of capsaicinoid extracts from pepper plants as an animal repellant. The patent discloses that compositions comprising these extracts repel animals based primarily on the unpleasant taste of the extracts. The patent further discloses that the extracts can be applied to objects to be protected using application vehicles, which include glues.

A deer repellent based on a bitter tasting compound, benzyldiethyl ammonium benzoate, is available under the name BITREX® (Macfarlan Smith Limited, Edinburgh, Scotland). The repellent is sold under the name TREE GUARD® (Becker-Underwood, Inc., Ames, Iowa) by various suppliers, including Itasca Greenhouse (Cohasset, Minn.; www.itascagreenhouse.com) and Treessentials (St. Paul, Minn.; www.treessentials.com). In addition to BITREX®, TREE GUARD® also contains latex, which adheres the BITREX® to surfaces to which it is applied, and provides water and sun resistance.

As an alternative to deterring or repelling wild animals by using unpleasant odors or tastes, mechanical devices have been devised. Such devices include fences, enclosures (such as greenhouse-type enclosures), containers for malodorous substances, and electrically-controlled devices that detect intrusion by an animal and emit a physical or electromagnetic deterrent.

One example of such a device is disclosed in U.S. Pat. No. 5,009,192, which teaches a device that comprises a motion sensor and water sprinkler. According to that invention, when an animal triggers the motion sensor, the sprinkler shoots a jet of water in the direction of the animal. The water jet, the noise of the sprinkler in action, or a combination of the two, frightens the animal into leaving the area.

Another example of a mechanical device to deter or repel wild animals from grazing on plants is disclosed in U.S. Pat. No. 5,892,446, which discloses a deterrent device that includes a motion sensor, a light source to illuminate the area to be protected, and a radio. In practice, the motion sensor detects an animal entering an area to be protected, activates the light source, and activates the radio. The light and the noise from the radio frighten the animal into leaving the area.

The chemical deterrents and repellents known in the art have been found by some to provide adequate protection from damage caused by wild animals. However, many are also offensive to humans and might be harmful to the environment in general. Likewise, many people have found the currently known mechanical means for deterring and repelling wild animals to be adequate. However, while such mechanical systems are often effective, they are relatively expensive per unit area protected, and suffer from the need to be continuously monitored to ensure that they are functioning properly. Thus, although numerous ways to deter or repel wild animals, such as wild herbivores, from eating or otherwise damaging trees, crops, flowers, fruits, and vegetables have been devised, alternative ways that provide superior deterrent or repellent effects are needed, particularly in view of the escalating damage caused by wild animals and the shortcomings of the systems currently available.

DISCLOSURE OF THE INVENTION

The present invention provides materials, compositions, methods, and kits for deterring or repelling animals. The invention can be used to deter or repel animals from eating plant material, including, but not limited to, fruit and vegetable plants, such as agricultural crops and plants grown in home gardens; trees, such as commercial forestry crops and trees planted in home lawns and gardens; and foliage and flowering plants, such as those planted in home flower gardens, landscaped areas, and flower nurseries. The plant material may be material in a growing or living state, or material after dropping from the plant, after harvesting, after processing, or after purchase by a person. Thus, the plant material can be corn, including corn kernels, before and after harvesting, and including forms prepared as feeds for animals, such as birds. Likewise, it can be sunflowers, including sunflower seeds, before and after harvesting and packaging for use as animal feed. It can further be any other plant material that can be used in a feed for animals, such as birds.

According to the invention, materials for deterring and/or repelling animals include particulate materials that interfere with an animal's ability to eat. According to the invention, compositions generally comprise at least one particulate material or at least one adherent and at least one particulate material. The methods of the invention generally comprise providing at least one particulate material, and applying the particulate material to the surface, interior, or both, of a plant material. In embodiments, the methods comprise providing at least one adherent and at least one particulate material, and applying both to a plant material that is typically eaten by one or more animals. The kits of the invention generally provide at least one particulate material. In embodiments, the kits of the invention provide at least one adherent and one particulate material in at least one container.

In a first aspect, the invention provides a material for deterring or repelling animals. In general, this aspect of the invention provides at least one particulate material that is suitable for applying to the surface or the interior of a plant material.

As used herein, a particulate material, or particle, is any substance that is provided in granular particles approximately the size of sand particles, preferably large or coarse sand particles, or approximately the size of glass beads that are used as reflective pavement additives for highway paints and the like. For example, the particulate material can have an average particle size of from about 50 micrometers (50 μm) to about 4.75 millimeters (4.75 mm). In embodiments, the particulate material has an average particle size of from about 50 μm to about 1700 μm, such as from about 150 μm to about 850 μm, from about 185 μm to about 850 μm, from about 300 μm to about 1400 μm, from about 710 μm to about 1400 μm, from about 1000 μm to about 1400 μm, from about 1180 μm to about 1400 μm, or from about 1180 μm to about 1700 μm. In other embodiments, the particulate material has an average particle size of from about 50 μm to about 500 μm. Exemplary particle sizes, or average particle sizes of large volumes of particles, are 50 μm, 100 μm, 125 μm, 150 μm, 180 μm, 250 μm, 300 μm, 425 μm, 500 μm, 600 μm, 710 μm, 850 μm, 1000 μm, 1180 μm, 1400 μm, and 1700 μm. Although any of the above sizes and ranges are suitable, it has been found that particles having a size of about 300 μm or greater, or about 710 μm or greater, such as from about 300 μm to less than about 1700 μm or about 710 μm to less than about 1700 μm, are generally suitable to deter numerous different species of herbivores. Particles of about any of the above sizes, compositions comprising particles having an average size of about any of the above sizes, or compositions comprising particles having a range of sizes defined by about any of the above sizes are encompassed by the present invention. These sizes reflect the diameter or length of the longest dimension of the particles. Particles according to the present invention are typically generally spherical in shape, although other shapes, including non-symmetrical shapes, are encompassed by the invention.

The average size of the particles, and the size distribution of particles within the size range, is not critical to practice of the invention as long as the materials and compositions of the invention contain a sufficient number of particles, when applied to a plant material, of adequate size to interfere with an animal's chewing if ingested. That is, any size particulate material, having any average size, is encompassed by the invention as long as the particulate material can be used in accordance with the invention. While not being limited to any single mechanism of action, it is believed that one likely way that the particles deter ingestion of treated plant material is by stopping the animal's upper and lower teeth from contacting each other, such contact being necessary for the animal to grind the plant material before swallowing. Thus, particles having a size sufficient to interfere with contact between an animal's upper and lower teeth are preferred. In addition, it is envisioned that biting down on the particles produces an irritation or pain on the teeth and gums, which deters the animal from further ingestion of plant material in the area of the treated plant(s). Thus, particles that are not crushed, pulverized, or otherwise destroyed by the force applied by an animal's jaws when chewing are preferred.

The particles can be made of any suitable material. Exemplary materials include sand, glass, rock, silica, crystalline forms of minerals, metal, plastic, and other man-made substances. The particulate material used in any particular aspect of the invention is not critical, and can be selected by one of skill in the art without undue experimentation. In embodiments, glass beads, such as those available under the VISIBEAD® name from Potters Industries (Potters Industries, Inc., 377 Route 17, Hasbrouck Heights, N.J. 07604; www.pottersbeads.com) are used. Such glass beads come in various average sizes. While any size (such as Type I, Type II, Type III, and Type IV VISIBEAD®) can be used, it has been found that beads of the same general size as Type III VISIBEAD® beads provide excellent deterrent effect while still being small and light enough to adhere to plant materials at a high rate. Likewise, particles of other materials having the same general size provide the same qualitative deterrent effect.

A specific particulate material, or combination of particulate materials, can be selected by the practitioner based on its properties (e.g., color, size) and the application (e.g., flowering plants in a home garden, commercial forestry). For example, it has been found that commercially available coarse sand is suitable for use in the invention, and is relatively inexpensive. While use of coarse sand to treat flowering plants in a home garden might result in plants that are unattractive to a homeowner, this unattractiveness is likely irrelevant in commercial forestry or agricultural crop applications. It has also been found that glass beads, such as those available from Potters Industries (www.pottersbeads.com) for highway marking, provide excellent repellent properties. Although glass beads are more expensive than sand, they provide an acceptable, if not enhanced, visual appearance for plants that have been treated, and are thus suitable for use on flowering plants in home gardens. In addition, it appears that such glass beads are not as easy for animals to see. This property appears to enhance the deterrent effect of the present materials, compositions, and methods by reducing animals' abilities to determine if plant materials have been treated. Other particulate materials might have other characteristics that are advantageous or suitable for particular applications, and can be selected based on those properties. One of skill in the art can select a suitable particulate material or combination of particulate materials for each specific application without undue experimentation.

In another aspect of the invention, compositions are provided. Compositions according to the invention comprise two or more different particulate materials or at least one particulate material and at least one adherent. Thus, in embodiments, compositions are provided that contain one or more adherent and one or more particulate materials. For example, compositions according to the invention can contain a single adherent and a mixture of two or more particulate materials. Likewise, the compositions can contain a mixture of two or more adherents and a single particulate material. Any combination of particulate materials or of adherents and particulate materials is envisioned as part of the present invention, as long as the particulate material(s) and adherent(s) are suitable for use in the methods of the invention. In a preferred embodiment, the compositions contain a single adherent and a single type of particulate material.

As used herein, an adherent is any substance that promotes adherence of a particulate material according to the invention to a plant material. It can be, but is not limited to, a substance that is at least slightly viscous or sticky when wet and hard when dry. The term adherent includes, but is not limited to, adhesives or glues (these two terms being used interchangeably herein). Specific substances that act as adherents are well known to those of skill in the art. Examples include, but are not limited to, polyvinyl acetate (PVA or "white glue"), aliphatic resins ("yellow glue"), rubber cement, polyurethane adhesive, epoxy adhesives, cyanoacrylate adhesives, acrylic sealers, spray glue (such as that available from the Elmer's Company, 3M, and others), various polymeric or polymer forming materials, latex, gums (e.g., plant gums), and the like. Other examples are adherents that can be used to coat, cover, or seal various objects. These adherents include, but are not limited to, paints (e.g., latex, enamel, alkyd), caulks, rubbers (e.g., natural and synthetic rubbers, such as silicone), liquid plastics, vinyls, epoxies, acrylic resins, wood enamels, wood preservatives (e.g., polyurethane), and oils, such as plant oils (e.g., linseed oil). Other examples include, but are not limited to, polybutene polymers, acrylic vinyl acetate copolymers, emulsified asphaltic materials, and aqueous acrylic polymers or polymer emulsions that dry upon spraying and exposure to the air. Additional non-limiting examples of suitable adherent substances are disclosed in U.S. Pat. Nos. 5,698,191, 4,065,577, 3,980,773, and 3,089,280, the disclosures of all of which are hereby incorporated herein in their entireties. Indeed, consumer products that provide adherent properties, such as hairsprays, are included among the adherents according to the present invention.

As is evident from the examples of adherents listed above, an adherent according to the invention can be one that, when applied or shortly thereafter, is sticky or tacky, but changes to a non-sticky or non-tacky consistency shortly after application (e.g., acrylic sealers, latex). Likewise, an adherent can be one that has a sticky or tacky consistency when applied and for an extended period of time thereafter (e.g., spray adhesive). Adherence can be accomplished by any known physical means, such as by hydrogen bonding (e.g., glues) or capillary attraction of viscous liquids (e.g., acrylic sealers and latex). The type of adherent and its particular setting properties can be selected by one of skill in the art without undue experimentation based on the needs for each specific application.

Any physical form of the adherent is contemplated by the invention. For example, the adherent may be a solid, as, for example, in the case of a glue stick. It also may be a liquid, as, for example, in the case of adhesives delivered from bottles or from aerosol dispensers.

Field tests have shown that many adherents, such as acrylic sealers and spray glues, to be particularly advantageous in all weather conditions, including humid or wet conditions. In addition, many adherents, such as latex, have been found to be advantageous where dry conditions prevail and where a minimally altered visual appearance of the treated plant material is not necessarily desired. Acrylic sealers and latex have been found to provide excellent water resistance. Thus, use of these types of adherents, or other water-resistant adherents, reduces the number of times the compositions need to be applied to the plants to provide satisfactory deterrent action throughout the growing season or time during which destruction by animals typically occurs. In addition, spray glue has been found to provide excellent adhesiveness.

A particular adherent, or combination of adherents, can be selected by the practitioner based on its particular properties (e.g., color/transparency, water resistance) and the specific application (e.g., flowering plants in a home garden, commercial forestry). For example, one might choose to use an acrylic sealer or a latex, which have superior water resistance properties, for commercial applications. On the other hand, one might choose to use a spray adhesive, which has excellent adhesiveness and dries clear, for home garden applications. In addition, if a large area were in need of treatment, one might choose to use a spray glue for one section (e.g., the perimeter) and an acrylic sealer or latex for another section (e.g., the interior). Furthermore, a mixture of an acrylic sealer or latex and a spray glue might be used to provide a very long-lasting effect that has superior adhesiveness. One of skill in the art can select a suitable adherent or combination of adherents for each particular application without undue experimentation.

The adherent, particulate material, or compositions comprising them can comprise additional components, including, but not limited to, solvents and diluents. For example, compositions can comprise agents that improve the flow characteristics, such that the adherents or particulate materials can be applied with less effort or such that they spread more or less quickly and extensively upon application to the plants. In certain situation, such as when application occurs from above (e.g., from an airplane), one might want the adherent to flow extensively before setting up to better ensure that portions of the plant near the ground will be covered. On the other hand, if application occurs from below, one might want the adherent to have minimal flow before setting up to minimize loss of adherent by dripping off the treated plant surfaces. In addition, in embodiments where adherent is applied before particulate material, one might want to include solvents or other additives that extend the time for setting up of the adherent to permit a larger area to be treated with adherent before the particulate material is applied. By adjusting the flow and set up characteristics, one can achieve an application that is best suited for each particular need.

Likewise, other animal repellents or deterrents can be included with the adherent(s), particulate material(s), or compositions comprising them. They can also be included in the methods and kits of the invention. As discussed above, many deterrents for wild animals are known in the art. The present invention contemplates inclusion of one or more of those repellents or deterrents in addition to the adherents and particulate materials, where desired. For example, an adherent or particulate material of the present invention can be formed into a composition that includes capsaicin or a capsaicinoid compound. Alternatively, or in addition, it can include other substances that animals, and in particular wild animals such as herbivores, find taste unpleasant, such as BITREX®.

Insect, grub, slug, snail, or other pest repellents, deterrents, or poisons can also be included in the compositions, methods, and kits of the invention. Numerous repellents, deterrents, and poisons are known in the art, as are useful amounts and protocols for applying. Any suitable repellent, deterrent, or poison can be included without undue experimentation by one of skill in the art.

In general, any amounts of particle(s), adherent(s), and optional additional component(s) can be combined so long as a sufficient number of particles are provided to achieve a repellent or deterrent effect when applied to plant material, and there is sufficient adherent to adhere the particles to the plant material, where adherent is used. The practitioner may select amounts based on the number of animals to be deterred, the amount of area or number of plants to be treated, or any other consideration.

In another aspect, the present invention is directed to a method of treating plant material to deter animals from eating the plant material. The method of the invention can be practiced in various ways. In its basic form, the method comprises applying a particulate material to the plant material. The method can further comprise providing the particulate material in various forms, including, but not limited to, an untreated form or a form that has been treated with an adherent. The method can comprise further steps as well, such as providing and applying an adherent, and providing and applying a substance that covers the particulate material or particulate material and adherent.

As used herein, plant material is any part of a plant. This includes, but is not limited to, roots, trunks, stems, shoots, leaves, flowers, fruits, and seeds or seed cases. It is envisioned that the compositions of the invention will primarily be applied to any portion of a plant that is typically bitten, gnawed, or eaten by an animal. As mentioned above, plant material includes materials that are no longer attached to a living plant, and thus include fallen fruits or vegetables, harvested fruits and vegetables, harvested seeds or seed pods, and other plant materials that are known to be consumed by humans or animals. Exemplary plant materials include, but are not limited to, flowers and ground covers, such as lilies, daylilies, hostas, cannas, irises, begonias, zinnias, petunias, daisies, tulips, poppies, sunflowers, cosmos, asters, dahlias, liriope, phlox, ivy, ferns, and the like; flowering trees, such as dogwoods, tulip poplars, magnolias, and the like; evergreen trees, such as firs, cedars, pines, hollies, and the like; fruits and fruit trees, such as apples, peaches, pears, cherries, and the like; hardwood trees, such as oaks, maples, walnuts, cherries, ash, and poplars; berries and berry plants and bushes (including both thorny and thornless), such as strawberries, blueberries, blackberries, raspberries, and the like; shrubs, such as rhododendrons, azaleas, hollies, and the like; and vegetables, gourds, and melons, such as beans, peas (e.g., English peas, crowder or blackeyed peas), lettuce, greens, beets, turnips, corn, tomatoes, zucchinis, summer squash, cantaloupes, watermelons, honeydews, and the like.

Accordingly, the method can be used to treat living plant material (i.e., material that is still associated with the plant) or plant material that is no longer associated with the plant from which it came (e.g., fallen fruit, harvested fruit, harvested vegetables, seeds).

Applying the particulate material and, optionally, the adherent, according to the invention deters and/or repels animals from eating the plant material. In certain instances, it also deters and/or repels animals from eating untreated portions of the plant and untreated plants surrounding the treated plant. The deterrent effect can be short-lived (e.g., about one week) or long-lived (e.g., one month or more). In general, the effect is maintained at least as long as the particulate material is embedded in or adhered to the plant material, and can be as long as a whole growing season or a year or more. When used on post-harvest products, the effect can continue for as long as the product is present.

The method according to the invention comprises applying at least one particulate material to a plant material. Applying can be accomplished in many ways. In its most basic form, applying of the particulate material can be accomplished by either of two ways. Applying can be accomplished by inserting or embedding the particulate material into the plant material, such as by pushing (manually or with a tool or machine), shooting (using a gun or other device that provides sufficient force to embed the particulate material in the plant material), or injecting (using a syringe, etc.). While not providing any distinct advantage over untreated particles, particles that have been coated with adherent can be inserted into plant material. Applying can also be accomplished by adhering the particulate material onto the surface of the plant material. Such adhering can be accomplished by coating the particulate material with an adherent, then applying the particulate material to the surface of a plant material. It can also be accomplished by applying an adherent to the plant material before or at the same time as applying the particulate material.

In embodiments, at least one particulate material is inserted into a plant material and also applied to the surface of the plant material. In other embodiments, at least one first plant material of a plant is treated by insertion of at least one first particulate material into the first plant material, while at least one second plant material of the plant is treated by adherence of at least one second particulate material onto the second plant material. In preferred embodiments, the at least one particulate material comprises a glass bead.

In exemplary embodiments of the method of the invention, the method comprises providing at least one adherent and at least one particulate material, and applying the adherent and particulate material to a plant material. Generally speaking, this embodiment of the invention can be practiced using two different configurations of adherent and particulate material. In one embodiment, referred to as the "two-step" process, the adherent and particulate material are provided as two separate components. In practicing this configuration of the method, the adherent is first applied to the plant material to be treated, then the particulate material is applied while the adherent is still wet or otherwise capable of adhering the particulate material. Upon contact with the adherent, and, if necessary, drying, curing, or setting up of the adherent, the particulate material is adhered to the treated plant material. In accordance with the discussion above regarding adherents and particulate materials, any combination of one or more adherent and one or more particulate material can be used in this configuration of the method of the invention.

In the second configuration, referred to as the "one-step" process, the adherent and particulate material are combined prior to or at the time of being applied to the plant material. The combination is applied, and, upon drying, curing, or setting up of the adherent (if necessary), the particulate material is adhered to the treated plant material. Any of the compositions of the invention discussed above or otherwise contemplated by the invention that comprise an adherent can be applied in the one-step method.

Any suitable way of applying the adherent and particulate material can be used in the method of the invention. For example, aerosol spraying of adherent coupled with manual distribution or application (e.g., casting, dropping, sprinkling) of the particulate material can be used. Likewise, manual pumps, such as garden sprayers available at home improvement and garden centers, can be used to apply the adherent, particulate material, or combination. In addition, pressure-assisted delivery devices, such as pneumatic or hydraulic sprayers, can be used. Also, adherent and/or particulate material can be brushed or rubbed onto the plant material. Furthermore, large-scale application techniques, such as delivery from an airplane or helicopter as a dump, spray, or mist can be used. Treatment can also be effected by dipping a plant material into a composition comprising at least one adherent, then into a composition comprising at least one particle, or by dipping into a composition comprising at least one adherent and at least one particle. Aerosol sprays, manual pumps, brushing, rubbing, and pressure-assisted delivery devices, and techniques for large-scale application of liquid materials to forestry or agricultural crops are known in the art, and any of these suitable techniques can be used.

In embodiments, a relatively thick coating of adherent and particulate material is applied to plant material. The thick coating is advantageous in many situations, such as when there is heavy and repeated damage to the treated plants or when heavy or frequent rain is expected. In other embodiments, a relatively thin coating of adherent and particulate material is applied to plant material. The thin coating is advantageous in many situations, such as when the plants are present for their visual appeal (e.g., in a home flower garden), when the plant is near to harvest, when the plant is not subject to heavy grazing, or when the plant is surrounded by other plants that have been treated. The varying thicknesses of coatings can be achieved by varying the number of applications of the adherent, the amount of particulate material, or both. Alternatively, various thicknesses can be achieved by adjusting the characteristics of the adherent.

In embodiments, only certain parts of a plant is treated, or different parts of a plant are treated differently than others. For example, when only the flowering portion of a garden flower is eaten by animals, only that portion of the plant might be treated. Likewise, if only the bark of a tree is eaten, then only the bark might be treated. Alternatively, if the bark and new shoots of a tree are eaten, then these two areas might be treated. Alternatively, if visual appearance of the plant material is of great importance, the underside of leaves of the plant, or some other inconspicuous portion of the plant, may be treated. In addition, if visual appearance of the plant material is of great importance, relatively few particles might be applied to visually conspicuous portions of the plant while a greater number are applied to less conspicuous places. In this way, the deterrent/repellent effect is still achieved, yet the treatment is undetectable under normal conditions. One can envision numerous combinations of treatments, with numerous different adherents, particulate materials, and combinations, and numerous different flow and thickness characteristics, and additives. All of these combinations are included within this invention.

In yet other embodiments, plant materials that are not intended for human consumption are treated. These materials can include plant leaves and portions of flowering trees, garden flowers, etc. They can also include seeds and seed pods, such as sunflower seeds (with or without shells), corn (on the ear or as individual kernels or a cracked corn), thistle seeds, saffron seeds, which are to be used as feed for wild animals, such as birds. In these embodiments, the plant materials can be treated while still attached to the plant. However, it is preferred that the plant materials be treated after processing, for example, as a last step before packaging for sale. For example, an adherent and particulate material can be applied to sunflower seeds or cracked corn just prior to packaging for sale as bird food. The particulate material, adhered to the seed or corn, will then be packaged with the seed or corn, and will be present when the seed or corn is placed in a bird feeder or spread on the ground. Animals other than birds that might ingest the seed or corn will ingest the particulate material, and it will have the same effect on the animal as if the animal had ingested a treated leaf or flower. The unpleasant effect will deter the animal from further eating the seed or corn. Furthermore, any particulate material that might be consumed by a bird would not be harmful to the bird, and might even benefit the bird by serving the function of a grinding stone in the digestive tract.

The compositions and methods of the invention are well suited for deterring animals from eating the treated plant material, other parts of plants that have had material treated, and other plants in the general area of treated plant material. They are also well suited for repelling animals from the treated plant material, other parts of plants that have had material treated, and other plants in the general area of treated plant material. It is to be understood that all animals that ingest the treated plant materials will be deterred and repelled. Exemplary animals that are deterred and/or repelled are herbivores, including ruminants. Animals include, but are not necessarily limited to, deer, moose, elk, caribou, rabbits, groundhogs, raccoons, skunks, opossums, squirrels, chipmunks, beavers, gophers, voles, mice, rats, nutria, muskrats, kangaroos or other marsupials, and the like. As can be seen, rodents that are known to cause damage to vegetables, fruits, and flowering plants are also among the animals that can be deterred or repelled by the present compositions and methods.

In general, treatment of living plant material in accordance with the present invention has no apparent lasting deleterious effect on the biological processes of the treated plants. That is, the treated plants appear to continue to grow, bud, flower, etc. at the same rate or about the same rate as other, untreated plants. Thus, it appears that all essential biological processes, such as transpiration, oxygen uptake, and photosynthesis, continue after treatment. While various components that may be selected for use in the compositions might have short-lived deleterious effects (e.g., organic solvents might cause whitening, yellowing, or browning of certain plant materials), the practitioner can avoid or minimize such components where these deleterious effects are unacceptable.

Because the adherents and particulate materials ultimately wash off of the treated plant material, plant material that is intended for human consumption can be treated without great concern for human safety. That is, adequate washing of the edible portions of the plants will remove all adherents and particulate materials before human consumption of the plant material. Furthermore, if adherent and particulate material is applied only to the exterior of the edible portions of the plants, peeling or otherwise removing the skin of the edible portion will remove the particulate material. In addition, care may be taken to treat only non-edible portions of the plants, or to treat only selected plants within a given area, and then remove the treated plants before harvesting of the entire area.

As discussed above, in general, any amounts of adherent, particle, and optional additional component(s) can be combined and applied to plant material, so long as a sufficient number of particles are adhered to or embedded in the treated plant material to achieve a repellent or deterrent effect, and there is sufficient adherent to adhere the particles to the plant material, when used. The practitioner may select amounts based on the number of animals to be deterred, the amount of area or number of plants to be treated, or any other consideration. For example, to deter deer, rabbits, and groundhogs from eating flowering plants in a home garden, one or two short bursts of spray adhesive can be applied to a plant material, and about 0.1 g of particles can then be applied to the plant material. For larger areas, adherent can be applied at a rate of about 3.78 liters per 37.16 square meters, and particles at a rate of about 0.01 to 0.5 g per plant. As discussed above, suitable amounts of each particular adherent(s) and particle(s) can be determined by one of skill in the art without undue experimentation.

Because the adherents and particulate materials are subject to washing off by rain, watering, etc., and subject to dislodging by mechanical forces, such as wind, brushing against other plants, etc., and because the adherents can be subject to chemical breakdown over time, the method of the invention can include re-applying of the adherent and particulate material periodically. Applying can be performed on a regular basis, for example once a week, once every two weeks, etc., once a month, once every two months, etc., or on an as-needed basis, for example after a particularly heavy rainfall, after a period of successive rainfalls, when inspection of the treated plants shows that some or all of the particulate material has been removed from the treated areas, or when damage to the treated plants by foraging is observed.

In embodiments, the method comprises providing and applying a coating that covers the adherent and particulate material after they have been applied to a plant material. For example, the method can comprise applying a spray adhesive and glass beads, then applying an acrylic sealer, latex, or other water-resistant substance, such as a wax-based product. Application of the coating provides additional benefits, such as enhanced water resistance, resistance to degradation from the sun's rays (e.g., UV protection), and enhanced resistance to physical removal of the particles. Any suitable sealer can be used, including, but not limited to, commercially available wood treatment products such as water sealers from the Thompson's company, the Wolman's company, Behr, and others. These coating materials can include any type of water resistant or repellant substances, including, but not limited to, waxes, oils, and silicones.

While not wishing to be limited to any single reason why the invention is effective at deterring and repelling animals, it is believed that treatment of plants in accordance with the invention results in plant material that is so unpleasant or unproductive to consume that animals that ingest it once do not return to attempt to eat the plant again, or attempt to eat other plants in the same area as the treated plant. The particulate material, and the combination of adhesive and particulate material, when applied to plant material and consumed, appear to render the plant material indigestible. It is believed that one likely way that the particles deter ingestion of treated plant material is by stopping the animal's upper and lower teeth from contacting each other, which is necessary for the animal to grind the plant material before swallowing. In this scenario, the plant material is not macerated into small enough pieces for digestion to effectively occur. In addition, it is believed that the particles, and the adherent and particle combinations, are unpleasant to the animal's mouth. Specifically, it is envisioned that biting down on the particles produces an irritation or pain on the teeth and gums, which deters the animal from further ingestion of plant material in the area of the treated plant(s). Further, it appears that the particles remain in contact with the mucous lining of the mouth (e.g., the lining of the cheek, gums, and tongue) even after swallowing, and cannot be removed easily by use of the tongue. The prolonged presence of the particles in the mouth causes irritation and can interfere with chewing of plant material consumed at a later time. The effects of the particles are particularly well suited for deterring ruminants, such as deer, because these animals regurgitate and re-chew ingested food multiple times before it is finally moved to the intestines for absorption into the animal's body.

Regardless of the precise way in which the particulate material or the combination of adherent and particulate material affects the animal, it has been observed that animals that eat treated plant material do not return to eat the treated plant again. It is assumed that the experience is so unpleasant or nutritionally unproductive that the animal, which remembers the particular plant or area, avoids the plant altogether in the future. Indeed, it is believed that ingestion of the particles or the adherent and particle combination is sufficiently unpleasant that animals that ingest it from one treated plant will avoid other plants that are treated in accordance with the invention without having to sample those other plants first. It appears that the mere chance that a plant might be treated in accordance with the present invention is sufficient to deter or repel an animal.

It does not appear that an animal that ingests the compositions or treated portions of plants is killed. Rather, feeding is unproductive and/or the animal's mouth is irritated by the ingested particles, and the animal is discouraged from returning to the particular plant or entire area. Accordingly, humans or animals who do not ingest the treated plant material are not harmed or offended by the compositions or treatments if they come in contact with the treated plants. This is an advantage over many other deterrents and repellents known in the art.

In yet another aspect, the invention provides kits. In general, the kits include at least one particulate material. In preferred embodiments, the kits comprise at least one adherent and at least one particulate material of the invention. In embodiments, the kits include all of the components needed to practice one or more embodiment of the methods of the invention. Ancillary components are also included in certain embodiments of the kits, as are instructions for using the materials in the kit in accordance with the invention.

In one embodiment of the kit, at least one adherent and at least one particulate material are provided separately in a packaged combination (i.e., in a single package). That is, at least one adherent is contained in a first container, and at least one particulate material is contained in a second, different container, both being included in a single package. Multiple containers of adherent and/or particulate materials can be included in a single kit to permit the practitioner to make various volumes of materials to be applied to plants, to perform multiple treatments without having to obtain multiple kits, and to make various combinations of adherent, particulate materials, and compositions.

In accordance with the discussion above, multiple adherents and particulate materials can be provided in a single kit. In such a situation, each adherent can be contained in its own container and each particulate material can be contained in its own container. In this way, the practitioner can select the appropriate adherent, particulate material, or combination of adherent(s) and particulate material(s) for the specific application needed. Alternatively, mixtures of two or more adherents or two or more particulate materials can be included in a single container, along with other mixtures in other containers or along with individual adherents in their own containers and individual particulate materials in their own containers. As discussed above, any combination of adherent(s) and particulate material(s) are included within the invention.

In another embodiment, at least one adherent and at least one particulate material are provided together in a packaged combination. That is, at least one adherent and at least one particulate material are contained in a single container within the kit. Providing the two together in the kit eliminates the need for the practitioner to combine them after opening the kit, and can reduce the time needed to practice the methods of the invention, or minimize errors in measuring the components or loss of materials due to spills, etc. In addition, it permits the practitioner to practice the "one-step" method without having to combine the adherent(s) and particle(s) prior to applying them to a plant material. As with other embodiments, kits according to this embodiment can include multiple containers within the kit, each container containing the same materials, different materials, or a combination where some containers contain the same material as others, while some containers contain unique contents.

In a preferred embodiment, the kit contains a spray adhesive in a first container and glass beads in a second container. The spray adhesive is preferably a water-based adhesive. It is preferably contained in a metal spray can. The glass beads are preferably contained in a plastic bag. In embodiments, multiple (e.g., two, three, four, five, six) containers of spray adhesive are included in the kit. In embodiments, multiple (e.g., two, three, four, five, six) containers of glass beads are included in the kit. In embodiments, gloves are also included. In yet other embodiments, a dispenser cup suitable for sprinkling of the glass beads is included in the kit.

In another preferred embodiment, the kit contains a latex adherent in a first container and glass beads in a second container. The latex adherent is preferably a water-based latex. It is preferably contained in a metal or plastic container that is, or can be, adapted to function as a pump sprayer. The glass beads are preferably contained in a plastic bag. In embodiments, multiple (e.g., two, three, four, five, six) containers of latex adherents are included in the kit. In embodiments, multiple (e.g., two, three, four, five, six) containers of glass beads are included in the kit. In embodiments, gloves are also included. In yet other embodiments, a dispenser cup suitable for sprinkling of the glass beads is included in the kit.

In yet another preferred embodiment, the kit contains an acrylic sealer adherent in a first container and glass beads in a second container. The acrylic sealer adherent is preferably a water-based acrylic sealer. It is preferably contained in a metal or plastic container that is, or can be, adapted to function as a pump sprayer. The glass beads are preferably contained in a plastic bag. In embodiments, multiple (e.g., two, three, four, five, six) containers of acrylic sealer are included in the kit. In embodiments, multiple (e.g., two, three, four, five, six) containers of glass beads are included in the kit. In embodiments, gloves are also included. In yet other embodiments, a dispenser cup suitable for sprinkling of the glass beads is included in the kit.

As can be seen from the above discussion, where desired, additional components can be included in the kits. For example, solvents or diluents for the adherent(s) can be included. Likewise, thickeners, binders, colorants, odorants, insecticides, fertilizers or other plant nutrients, and the like can be included in the kits. Furthermore, materials for measuring or delivering the components of the kit can be included. For example, measuring or mixing buckets, cups, spoons, etc., stirring bars, rods, etc., gloves (e.g., latex or plastic gloves), and the like can be included. In addition, equipment for delivering the adhesives and particulate materials of the invention, such as sprinklers, shakers, sprayers, and brushes, can be included in the kits. Each of these additional components, etc. can be included in packages of one or more item, or can be included as separate, unpackaged items.

A container can be anything that is suitable for containing the adherent(s), particulate material(s), and optional additional components to be contained. Thus, containers for the adherents can be, but are not limited to, cans or jars, such as those made of metal, plastic, rubber, and glass. The containers for the particulate materials can be, but are not limited to, cans, jars, or bags, such as those made of metal, plastic, rubber, glass, and fabric. In embodiments, the container can be the delivery device, such as a can suitable for sprinkling glass beads or coarse sand. The containers are preferably re-sealable or automatically sealing to preserve unused contents after initial opening.

The kits themselves can be fabricated from any suitable material, such as cardboard, plastic, metal, or glass. Cardboard and plastic are preferred materials for the kits.

Instructions for using one or more components of the kit, or for practicing the methods of the invention, may be included in the kit. The instructions may be provided as a separate component, such as printed material on a paper, card, plastic sheet, or the like. Alternatively, the instructions may be provided on the kit itself, for example, on a side or the top or bottom of the kit. Alternatively, the instructions may be provided on a container for a component of the kit.

EXAMPLES

The invention will be further described by the following examples, which are intended to be purely exemplary of the invention and should not be construed as limiting the invention in any way.

Example 1

Use of Spray Adhesive and Glass Beads on Leaves, Flower Buds, and Flowers in a Home Garden Materials: Spray adhesive from Elmer's® company; standard highway marking spheres from Potters Industries, Inc. having an average size of between about 300 µm and 1400 µm.

In a home garden containing a mixture of over 2,300 flowering plants, primarily daylilies and hostas, selected leaves and flower buds of the plants were treated as follows: At least one leaf or flower bud of approximately 80% of the plants was individually treated by applying sufficient spray adhesive to wet the leaf or flower bud. Approximately 0.1 g of glass beads were then applied, by manually sprinkling, to the adhesive-coated leaves and/or buds. Under the conditions used, from about 1 to about 50 beads became adhered to each plant material treated. The treated plant materials were not noticeably different in appearance from a distance of 5 meters. When observed at a distance of one meter or closer, the treated plant materials appeared slightly shiny (due to the adhesive) and the individual glass beads could be seen.

Within the first week after applying the glass beads, numerous deer were observed foraging on the plants. However, unlike the foraging that occurred before treatment, in which large portions of leaves and flower buds were eaten, after treatment the deer were observed to take one bite, but no more, from a treated leaf or flower bud. The vast majority of bites were taken from plants along the outer fringe of the garden. Within ten days after treatment, deer were observed to enter the area of treated plants but not graze on the treated plant material, other plant material from the same plant, or untreated neighboring plants.

Of tens of thousands of daylily blooms and flowers present in the garden, about 50 were eaten or bitten after treatment. In previous years, most of the daylily blooms and flowers were eaten by animals. In addition, of several hundred hostas in the garden, fewer than 20 blooms were eaten or bitten after treatment, whereas in previous years, most of the hosta plants (blooms, stalks, leaves) were essentially completely eaten.

The garden was treated as described above during three consecutive growing seasons (i.e., three years in a row during late spring, summer, and early fall). The results observed were similar each season.

In contrast to the results obtained for the treated garden, three untreated hostas in a small, separate garden having no treated plants were completely destroyed within the same time period as the observations on the treated plants and garden were being made. The results indicate not only that the treatment is capable of deterring animals from eating treated plants, but also that it deters them from eating untreated plants in the same general area.

Example 2

Use of Spray Adhesive and Glass Beads on the Underside of Daylily and Hosta Leaves Materials: Spray adhesive from Elmer's® company; standard highway marking spheres from Potters Industries, Inc. having an average size of between about 300 μm and 1400 μm.

In a home garden containing a mixture of over 2,300 flowering plants, primarily daylilies and hostas, selected leaves of daylilies and hostas were treated as follows: The underside of a leaf of one or more plants was individually treated by applying sufficient spray adhesive to wet the underside of the leaf. Approximately 0.1 g of glass beads were then applied, by manually sprinkling, to the adhesive-coated leaf. Upon returning the leaf to its natural position, it was not possible to detect which leaves had been treated. Based on the amount of grazing on leaves treated in this manner, it appeared that this treatment is as effective at deterring grazing by herbivores as the treatments described in Example 1.

Example 3

Use of Latex Adherent and Glass Beads on Leaves in Home Garden

Materials: Commercially available spray latex; standard highway marking spheres from Potters Industries, Inc. having an average size of between about 300 μm and 1400 μm.

In a home garden containing a mixture of over 2,300 flowering plants, primarily daylilies and hostas, selected leaves of hosta plants were treated as follows: At least one leaf or flower bud of approximately 10 of the hostas were individually treated by applying sufficient latex adherent to wet the leaf. While the latex was still wet, approximately 0.1 g of glass beads were then applied, by manually sprinkling, to the latex-coated leaves. Upon drying of the latex, the leaves appeared normal when viewed from about 5 meters. Close inspection (1 meter or closer) revealed the presence of the glass beads adhered to the leaf surfaces. Although fewer beads were observed to be adhered to each leaf than were adhered using the spray adhesive in Examples 1 and 2, a sufficient number of beads were adhered to deter grazing by animals. In summary, the results of the treatment were similar to those observed in Examples 1 and 2.

The latex and glass bead treatment was repeated on other hosta leaves within the garden late in the day on a day with high humidity, followed by a night with a heavy dew. Individual treated leaves were not detected when viewed from about 5 meters. However, upon inspection of the treated leaves at close distance (1 meter or closer), the leaves appeared to have a white haze on them, presumably a result of mixing of the latex with water before the latex dried. Fewer glass beads were adhered to the treated leaves than when the latex was applied in dry weather (and when spray adhesive was used, as in Examples 1 and 2). However, a sufficient number of beads were adhered to deter grazing by animals. In addition, it was observed that applying the latex and beads in moist or wet weather resulted in a treatment that did not set up as well as when applied in dry weather, resulting in a treatment that was not as long-lived as treatments performed in dry weather or with spray adhesive. However, treatment with latex in moist or wet weather still provided a deterrent and repellent effect. Thus, if a long lasting or clear treatment is desired, treatment with latex should be performed early in the day, preferably on a dry or rainless day.

Example 4

Use of Spray Adhesive and Sand

Materials: Spray adhesive from Elmer's® company; commercially available sand, having a size range from about 50 μm to about 4,750 μm. Sand individually tested included fine sand, medium sand, and coarse sand. Various colors of sand, including white, natural (tan), and green, were tested individually. Unless otherwise stated, results of various colors and sizes were substantially similar.

In a home garden containing a mixture of over 2,300 flowering plants, selected leaves of daylilies and hostas were treated as follows: At least one leaf of approximately 20 of the plants were individually treated by applying sufficient spray adhesive to wet the leaf. Approximately 0.1 g of sand were then applied, by manually sprinkling, to the adhesive-coated leaves. After treatment, the leaves appeared sandy or dirty when viewed from about 5 meters. Close inspection (1 meter or closer) revealed the presence of the sand adhered to the leaf surfaces.

Leaves treated with fine sand (about 50-100 μm in size) appeared to deter grazing by deer minimally, if at all. It is believed that, while fine sand might be unpleasant to the deer, it does not interfere to a great extent with chewing, or cause great discomfort to the teeth and/or gums.

Leaves treated with medium or coarse sand (greater than about 100 μm in size) had a significantly better deterrent effect than fine sand. It is believed that the improvement is related to improved interference with chewing, and increased discomfort to the teeth and/or gums.

After treatment with adhesive and sand, the plants had noticeably altered appearances. It was observed that untreated plants were subject to more grazing than treated plants within the same vicinity. It is believed that the deer and other animals that grazed on the plants could identify which plants had been treated and which had not, and were not deterred from eating the untreated plants. Thus, while the animals were deterred from eating treated plant materials, they were not significantly deterred from eating surrounding, untreated plants. Such an effect is in contrast to the effect seen with glass beads in the Examples above, indicating that the animals do not see the glass beads, and are thus unable to differentiate treated from untreated plant materials. Accordingly, they are deterred from eating all plant materials treated with glass beads, and repelled from the area containing the treated plant materials.

Example 5

Use of Spray Adhesive and Sandblasting Particles of Several Types

Materials: Spray adhesive from Elmer's® company; commercially available sandblasting particles of several types (mortar sand of various sizes and colors, including black, etc.), having a size range from about 500 μm to about 4,750 μm.

In a home garden containing a mixture of over 2,300 plants, selected leaves of daylilies and hostas were treated as follows: At least one leaf of approximately 20 of the plants were individually treated by applying sufficient spray adhesive to wet the leaf. Approximately 0.1 g of sandblasting sand were then applied, by manually sprinkling, to the adhesive-coated leaves. After treatment, the leaves appeared blackened and dirty when viewed from about 5 meters. Close inspection (1 meter or closer) revealed the presence of the sand adhered to the leaf surfaces.

Leaves treated with sandblasting sand deterred grazing by deer and other animals to substantially the same extent as coarse sand (Example 4).

Example 6

Use of Spray Adhesive and Silica Beads

Materials: Spray adhesive from Elmer's® company; commercially available silica beads (typically available as a drying agent, such as for flowers).

In a home garden containing a mixture of over 2,300 plants, selected leaves and flower buds and blooms of daylilies and hostas were treated as follows: At least one leaf or flower bud or bloom of approximately 20 of the plants were individually treated by applying sufficient spray adhesive to wet the leaf, bud, or bloom. Approximately 0.1 g of silica particles were then applied, by manually sprinkling, to the adhesive-coated leaves, buds, or blooms.

Leaves, buds, and blooms treated with this type of silica bead were consumed by animals to substantially the same extent as untreated plant materials. It is believed that this type of silica bead is too soft to be effective. That is, it appeared that the beads were crushed under the pressure of the animals' teeth, and thus were not effective at deterring the animals from eating the treated plants or repelling animals from the area of the treated plants.

Example 7

Use of Spray Adhesive and Fine Glass Beads

Materials: Spray adhesive from Elmer's® company; commercially available fine glass beads, having a size range from about 50 μm to about 150 μm.

In a home garden containing a mixture of over 2,300 plants, selected leaves of daylilies and hostas were treated as follows: At least one leaf of approximately 20 of the plants were individually treated by applying sufficient spray adhesive to wet the leaf. Approximately 0.1 g of glass beads were then applied, by manually sprinkling, to the adhesive-coated leaves. After treatment, the leaves appeared similar to untreated leaves when viewed from about 5 meters. Close inspection (1 meter or closer) revealed the presence of the beads adhered to the leaf surfaces.

Leaves treated with the fine beads appeared to deter grazing by deer minimally, if at all. The deterrent effect was similar to that seen with the fine sand reported in Example 4 (although the appearance of the treated plant materials differed). It is believed that, while these fine glass beads might be unpleasant to the deer, they do not interfere to a great extent with chewing, or cause great discomfort to the teeth and/or gums.

Example 8

Use of Acrylic Concrete Sealer and Glass Beads

Materials: Commercially available acrylic concrete sealer; standard highway marking spheres from Potters Industries, Inc. having an average size of between about 300 μm and 1400 μm.

In a home garden containing a mixture of over 2,300 plants, selected leaves of daylilies and hostas were treated as follows: At least one leaf of approximately 20 of the plants were individually treated by applying sufficient acrylic concrete sealer to wet the leaf. Approximately 0.1 g of glass beads were then applied, by manually sprinkling, to the adherent-coated leaves. After treatment, the leaves appeared similar to untreated leaves when viewed from about 5 meters. Close inspection (1 meter or closer) revealed the presence of the beads adhered to the leaf surfaces. Approximately 1 to 10 glass beads adhered to each adherent-treated surface. Generally and on average, the number of beads adhered to a leaf was less than the number adhered to a leaf to which a spray adhesive was applied (see Examples 1 and 2, for example). This result is due to the fact that the spray adhesive is relatively more sticky than the concrete sealer; thus, more particles adhere when spray adhesive is used. However, it has been observed that the presence of even a single particle on a plant material is sufficient to deter grazing by animals. Therefore, acrylic concrete sealers and other products with similar adherent properties can be used in accordance with the present invention.

Leaves treated with the beads deterred grazing by deer. Likewise, deer and other animals were deterred from grazing on other plants in the area of the treated plant materials. In addition, the treatment was highly water resistant, and provided a deterrent effect for extended periods. Furthermore, it provided the deterrent effect remained after rain.

Example 9

Use of Various Amounts of Latex and Glass Beads

Materials: Commercially available latex (for application of BITREX® deterrent); standard highway marking spheres from Potters Industries, Inc. having an average size of between about 300 μm and 1400 μm.

In a home garden containing a mixture of over 2,300 plants, selected leaves of daylilies and hostas were treated as follows: At least one leaf of approximately 20 of the plants were individually treated by applying varying amounts of latex to the leaf. Approximately 0.1 g of glass beads were then applied, by manually sprinkling, to the latex-coated leaves.

It was observed that relatively light application of the latex provided adequate adherent properties, which were substantially similar to the properties provided by the acrylic sealer used in Example 8. Increasing amounts of latex improved adherence of the beads to the plant materials. However, thick application of latex occasionally resulted in a white haze on the treated plant material upon drying.

All treatments were highly water resistant, and provided a deterrent effect for extended periods, even when subjected to rain.

Example 10

Use of Spray Latexes and Glass Beads

Materials: Commercially available spray latex and spray clear latex (Krylon brand); standard highway marking spheres from Potters Industries, Inc. having an average size of between about 300 μm and 1400 μm.

In a home garden containing a mixture of over 2,300 plants, selected leaves of daylilies and hostas were treated as follows: At least one leaf of approximately 20 of the plants were individually treated by applying varying amounts of spray latex or spray clear latex to the leaf. Approximately 0.1 g of glass beads were then applied, by manually sprinkling, to the latex-coated leaves.

It was observed that relatively light application of the latexes provided adequate adherent properties, which were substantially similar to the properties provided by the acrylic sealer used in Example 8. Increasing amounts of latex improved adherence of the beads to the plant materials. However, thick application of spray latex occasionally resulted in a white haze on the treated plant material upon drying. The spray clear latex was less likely to cause a haze upon drying.

All treatments were highly water resistant, and provided a deterrent effect for extended periods, even when subjected to rain.

Example 11

Use of Spray Clear Acrylic and Glass Beads

Materials: Commercially available spray clear acrylic latex (Krylon brand); standard highway marking spheres from Potters Industries, Inc. having an average size of between about 300 μm and 1400 μm.

In a home garden containing a mixture of over 2,300 plants, selected leaves of daylilies and hostas were treated as follows: At least one leaf of approximately 20 of the plants were individually treated by applying varying amounts of spray clear acrylic to the leaf. Approximately 0.1 g of glass beads were then applied, by manually sprinkling, to the acrylic-coated leaves.

The spray clear acrylic provided adequate adherent properties, which were substantially similar to the properties provided by the acrylic sealer used in Example 8. In addition, the acrylic dried clear, which is advantageous in a home garden setting.

All treatments were highly water resistant, and provided a deterrent effect for extended periods, even when subjected to rain.

Example 12

Use of Polyurethanes and Glass Beads

Materials: Commercially available water-based and solvent-based polyurethanes; standard highway marking spheres from Potters Industries, Inc. having an average size of between about 300 μm and 1400 μm.

In a home garden containing a mixture of over 2,300 plants, selected leaves of daylilies and hostas were treated as follows: At least one leaf of approximately 20 of the plants were individually treated by applying a sufficient amount of polyurethane to thoroughly wet the leaf. Approximately 0.1 g of glass beads were then applied, by manually sprinkling, to the polyurethane-coated leaves.

The polyurethanes provided adequate adherent properties, which were substantially similar to the properties provided by the acrylic sealer used in Example 8. In addition, the polyurethane dried clear, which is advantageous in a home garden setting. However, solvent-based polyurethanes often caused leaves to turn white.

Example 13

Use of Water Sealers as Cover for Adherents and Particles

Materials: Commercially available spray adhesive (Elmer's®); standard highway marking spheres from Potters Industries, Inc. having an average size of between about 300 μm and 1400 μm; commercially available deck waterproofers (e.g., Thompson's Water Seal®).

In a home garden containing a mixture of over 2,300 plants, selected leaves of daylilies and hostas were treated as follows: At least one leaf of approximately 20 of the plants were individually treated by applying a sufficient amount of spray adhesive to wet the leaf. Approximately 0.1 g of glass beads were then applied, by manually sprinkling, to the adhesive-coated leaves. Various waterproofing compositions (e.g., wax based, silicone-containing) were then applied to the leaves to cover the adhesive and beads.

While the waterproofers, alone, did not appear to be suitable for use as an adhesive because they were too thin (results of such field tests are not the subject of an Example herein), they proved to be suitable for providing waterproof characteristics when applied as a cover for adhesive/particle combinations. All treatments that included application of a waterproofer provided a waterproof deterrent effect for extended periods, even when subjected to rain.

Example 14

Treatment of Peach Trees with Spray Adhesive and Glass Beads

Materials: Spray adhesive from Elmer's® company; standard highway marking spheres from Potters Industries, Inc. having an average size of between about 300 μm and 1400 μm.

In a home garden containing peach trees, selected peaches were treated with spray adhesive and glass beads as follows: The peaches were individually treated by applying sufficient spray adhesive to wet a portion of the fruit. Approximately 0.1 g of glass beads were then applied, by manually sprinkling, to the adhesive-coated fruits. After treatment, the fruits appeared normal when viewed from about 5 meters. Close inspection (1 meter or closer) revealed the presence of the glass beads adhered to the fruits.

Inspection of the fruits over a four week period revealed that fewer than ten peaches were eaten or partially eaten by deer or raccoons. Several others appeared to have been eaten or partially eaten by squirrels. Inspection of fallen fruit revealed bites taken from several fruits, apparently by squirrels. No other marks were observed on any other fruits. During previous growing seasons, all fruits from the trees were typically removed, partially eaten, or bitten by deer and/or raccoons.

Ripe treated peaches were harvested. The skins were peeled from the fruits and the fruits consumed by a human without any unpleasant or deleterious effects.

Example 15

Treatment of Apple Trees and Fallen or Harvested Apples with Spray Adhesive and Glass Beads Materials: Spray adhesive from Elmer's® company; standard highway marking spheres from Potters Industries, Inc. having an average size of between about 300 μm and 1400 μm.

In a home garden containing apple trees, selected apples from a tree were treated with spray adhesive and glass beads as follows: The apples were individually treated by applying sufficient spray adhesive to wet a portion of the apple. Approximately 0.1 g of glass beads were then applied, by manually sprinkling, to the adhesive-coated fruits. After treatment, the fruits appeared normal when viewed from about 5 meters. Close inspection (1 meter or closer) revealed the presence of the glass beads adhered to the fruits. Fallen fruits were permitted to lie under the tree. Separately, five harvested apples were treated in the same manner. All five were placed under the treated apple tree. Two of the five apples were first cut open to reveal the interior.

After two weeks, minimal destruction of the apples on the tree occurred (two apples out of scores of apples on the tree were consumed). In addition, fallen fruit was not eaten (three apples fell during the test period, and none were touched by animals). Furthermore, the harvested, treated, and freshly cut apples were untouched. Fresh deer tracks were observed around the tree, fallen apples, and freshly cut apples, but no damage was observed.

Example 16

Treatment of Beans with Spray Adhesive and Glass Beads

Materials: Spray adhesive from Elmer's® company; standard highway marking spheres from Potters Industries, Inc. having an average size of between about 300 μm and 1400 μm.

In a home vegetable garden containing about 75 pole and bush bean plants, bean plants were treated with spray adhesive and glass beads as follows: The leaves of the bean plants were treated by applying sufficient spray adhesive to wet the leaf. Approximately 0.1 g of glass beads were then applied, by manually sprinkling, to the adhesive-coated leaves. After treatment, the leaves appeared normal when viewed from about 5 meters. Close inspection (1 meter or closer) revealed the presence of the glass beads adhered to the leaves. No significant damage to the bean leaves was observed throughout the growing season, and minimal damage to, or loss of, bean pods was observed.

Example 17

Treatment of Holly Trees and Bushes with Acrylic Sealer and Glass Beads or Sand

Materials: Commercially available acrylic concrete sealer; standard highway marking spheres from Potters Industries, Inc. having an average size of between about 300 μm and 1400 μm; commercially available sand.

In a home garden containing holly trees and bushes, the trees and bushes were treated as follows: Selected leaves up to about 2 meters (about 6 feet) from the ground were treated by applying sufficient acrylic concrete sealer to wet the leaves. Approximately 0.1 g of glass beads or 0.1 g sand per leaf were then applied, by manually sprinkling, to the adherent-coated leaves. After treatment, the leaves treated with glass beads appeared similar to untreated leaves when viewed from about 5 meters. Close inspection (1 meter or closer) revealed the presence of the beads adhered to the leaf surfaces. Approximately 1 to 10 glass beads adhered to each adherent-treated surface. After treatment, the leaves treated with sand appeared dirty or sandy when viewed from about 5 meters. Close inspection (1 meter or closer) revealed the presence of sand particles adhered to the leaf surfaces. Each treated surface contained numerous sand particles of different sizes. It was estimated that approximately 1 to 10 sand particles of a size between about 300 μm and 1,400 μm (coarse sand) adhered to each treated surface.

The treatment was performed early during the winter season, then repeated once at about the middle of the winter season. No significant differences between the deterrent effectiveness of glass beads and sand were observed.

It was observed that few, if any, of the holly tree and holly bush leaves were eaten during the first month after the first treatment. Inspection of the leaves after about six weeks indicated that many treated leaves no longer contained beads or coarse sand, so the acrylic sealer and particles were re-applied to the plants in the same manner and at the same rate. After re-application, few, if any, of the holly tree and holly bush leaves were eaten.

Treatment of the holly trees and bushes was performed over two consecutive winter seasons. Whereas in years preceding initiation of treatment, heavy damage by browsing of deer was observed, during the two years of treatment, the trees and bushes were essentially completely protected.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the following claims.

What is claimed is:

1. A method of deterring or repelling an animal from eating plant material by interfering with the animal's ability to chew the plant material, said method comprising applying to the plant material an adhesive and glass beads having an average size of between about 300 μm and 1400 μm,
   wherein the glass beads do not comprise a poison, and
   wherein biting of the glass beads by the animal interferes with the animal's ability to chew the plant material and deters or repels the animal from eating the plant material.

2. The method of claim 1, further comprising repeating the applying.

3. The method of claim 1, wherein the plant material comprises bird food.

4. The method of claim 1, wherein the method interferes with the animal's ability to eat the plant material.

5. A method of deterring or repelling a deer from eating plant material by interfering with the animal's ability to chew the plant material, said method comprising applying to the plant material a spray adhesive and glass beads having an average size of between about 300 μm and 1400 μm,
   wherein the glass beads do not comprise a poison, and
   wherein biting of the glass beads by the deer interferes with the deer's ability to chew the plant material and deters or repels the deer from eating the plant material.

* * * * *